United States Patent [19]

Schreiber

[11] Patent Number: 4,902,681
[45] Date of Patent: Feb. 20, 1990

[54] INHIBITION OF IMMUNE CLEARANCE USING PROGESTERONE ANALOGUES

[75] Inventor: Alan D. Schreiber, Philadelphia, Pa.

[73] Assignee: University of Pennsylvania, Philadelphia, Pa.

[21] Appl. No.: 89,790

[22] Filed: Aug. 27, 1987

[51] Int. Cl.$^4$ .............................................. A61K 31/56
[52] U.S. Cl. .................................... 514/177; 514/178; 514/885
[58] Field of Search ....................... 514/177, 178, 181; 435/13; 260/397.3

[56] References Cited

U.S. PATENT DOCUMENTS 3,463,852  8/1968  Reiman et al. ...................... 514/178
4,701,450 10/1987  Kelder et al. ...................... 514/177

FOREIGN PATENT DOCUMENTS 1124906 11/1984 European Pat. Off. ............ 514/177

OTHER PUBLICATIONS

Bach, J. F.; John Wiley & Sons (N.Y.); "Immunology", p. 812 (1982).
Roubinian et al.; Androgenic Hormones Modulate Autoantibody Responses and Improve Survival in Murine Lupus, J. Clin. Invest., 59:1066–1070 (1977).
Chem. Abs. 88:183384 Further Studies on the Angrogenic, Anti-Androgenic, and Synandrogenic Actions of Progestins, Bullock et al., (1978).
Chem. Abs. 81:33775 Inhibition of Lordosis Behavior in Overiectiomized Guinea Pigs by Mesencephalic . . . Morin et al., (1974).
Siiter et al.; Sex Steroids and the Immune System, J. Steroid Biochem., vol. 12, 425–432 (1980).
Duncan et al.; An In Vivo Study of the Action of Antiglucocorticoids on Thymus Weight Ratio, Antibody Titre and the Adrenal-Pituitary-Hypothalamus Axis, (1979), J. Steroid Biochem., vol. 10, 245–259.
Roubinian et al.; Effect of Castration and Sex Hormone Treatment on Survival, Anti-Nucleic Acid Antibodies, and Glomerulonephritis in NZB/NZW F$_1$ Mice; J. Exp. Med. 147, 1568–1583 (1978).
Nettle et al., "The Effect of Endogenous and Synthetic Steroids on the Clearance of IgG and/or C3 Coated Cells", *Blood 64*: Suppl. 1:88 A (Abstract) (1984).
Ahn et al., "Danazol for the Treatment of Idiopathic Thrombocytopenic Purpura", *N. Eng. J. Med. 308*: 1396–1399 (1983).
Schreiber et al., "Effect of Danazol in Immune Thrombocytopenic Purpura", *N. Engl. J. Med. 316*: 503–508 (Feb. 1987).
Jungers et al., "Hormonal Modulation in Systemic Lupus Erythematosis", *Arthritis Rheum. 26*: 1243–2150 (1985).
Friedman et al., "Effect of Estradiol and Steroid Analogues on the Clearance of Immunoglobulin G-Coated Erythrocytes", *J. Clin. Invest. 75*: 162–167 (1985).

Primary Examiner—H. M. S. Sneed
Assistant Examiner—J. Saba
Attorney, Agent, or Firm—Woodcock Washburn Kurtz Mackiewicz & Norris

[57] ABSTRACT

Clearance of antibody-coated cells from the circulation of mammals is inhibited by administering an effective amount of 17-hydroxyprogesterone or 16-methylprogesterone. The compounds are useful in treating autoimmune disease.

13 Claims, 1 Drawing Sheet

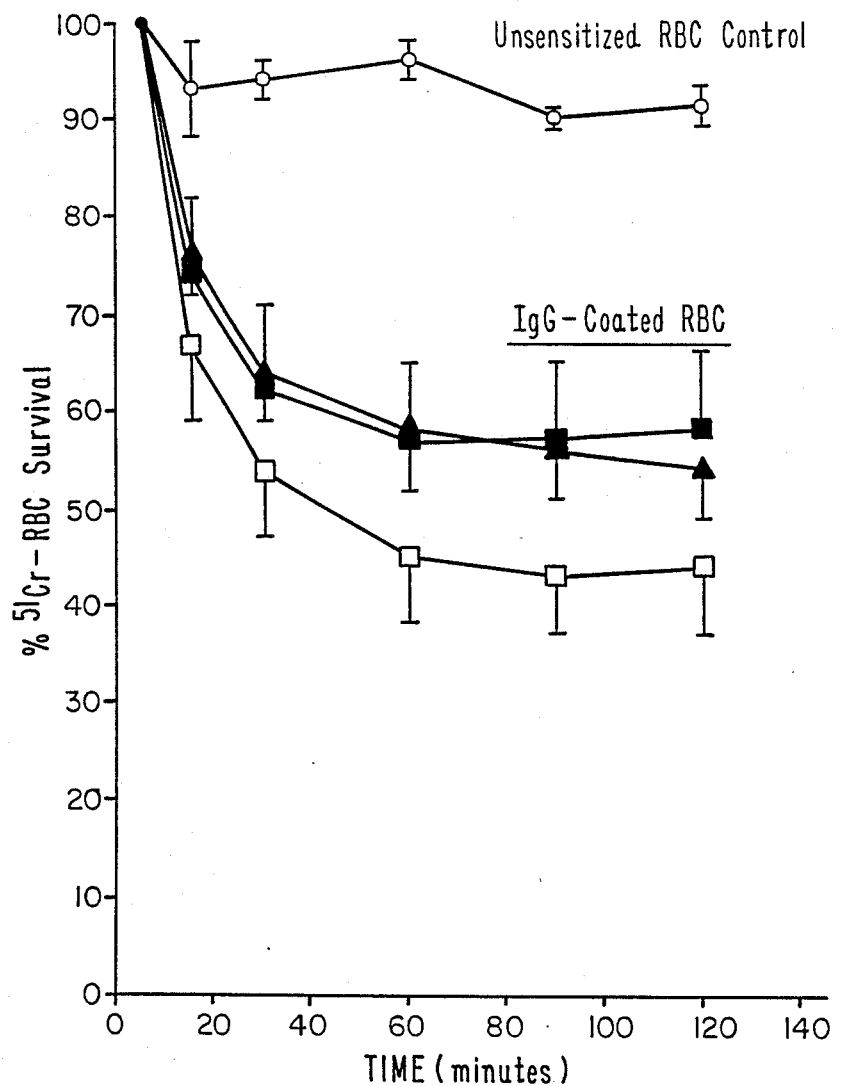

INHIBITION OF IMMUNE CLEARANCE USING PROGESTERONE ANALOGUES

REFERENCE TO GOVERNMENT GRANTS

The invention described herein was supported by National Institutes of Health grants AI-22193 and HL-28207. The Government has certain rights in the invention.

FIELD OF THE INVENTION

The invention relates to the treatment of autoimmune disease, and in particular to the inhibition of clearance of antibody-coated cells from the circulation of mammals.

BACKGROUND OF THE INVENTION

Corticosteroids inhibit clearance of IgG-coated erythrocytes by modulating splenic macrophage $F_c(IgG)$ receptor activity. They have been used in treating autoimmune disorders such as immune thrombocytopenic purpura and systemic lupus erythematosus. However, corticosteroids have undesirable side effects such as exacerbation of diabetes, hypertension, electrolyte imbalance, increased appetite and weight gain, moonlike faces, osteoporosis, myopathy and increased susceptibility to infection. The severity of these side-effects relates to both the duration and dosage of therapy.

It has been reported that progesterone has been observed to inhibit splenic macrophage clearance of IgG-coated erythrocytes by fifty percent. Nettl et al, *Blood* 64:Suppl 1:88 A (Abstract) (1984). However, progesterone is a progestational agent, and exerts substantial end-organ hormonal effects, making its use in treatment less practical.

The autoimmune disease chronic immune thrombocytopenic purpura has been treated with danazol, an antigonadotropic drug. Ahn et al, *N. Engl. J. Med.* 308: 1396–1399 (1983); Schreiber et al, *N. Engl. J. Med.* 316: 503–508 (1987). Danazol is a synthetic analogue of androgenic steroids and progesterone. As an androgen, danazol can cause masculinization. Moreover, use of this drug in treating systemic lupus erythematosus has been associate with a high incidence of side-effects such as a rise in hepatic enzymes, skin rash, weight gain, acne and myalgia. Dougados et al, *Arthritis Rheum.* (Suppl.) 28: S46 (1985); Jungers et al, *Arthritis Rheum.* 28: 1243–1250 (1985).

The synthetic hydroxyprogesterone derivative cyproterone acetate has been used in treating female patients having moderately active systemic lupus erythematosus. Jungers et al, supra. Cyproterone acetate is an antigonadotropic agent possessing peripheral antiandrogenic effects. As an antigonadotropic agent, it affords contraception in females.

Despite achieving some success in treating systemic lupus erythematosus, it is likely that cyproterone acetate has progestational activity, making it undesirable in treatment. Moreover, it has been reported that antigonadotropic drugs such as cyproterone acetate and danazol should not be used in male systemic lupus erythematosus patients. Jungers et al, supra. In males, the antigonadotropic effect of cyproterone acetate induces a marked decrease in plasma testosterone concentration. In addition, cyproterone acetate acts as an antiandrogen in displacing 5-dihydrotestosterone from a specific receptor in the prostate. According to Jungers et al, supra, administration of cyproterone acetate in male systemic lupus erythematosus patients should induce a marked fall in plasma testosterone level which could potentially provoke an exacerbation of lupus disease.

Danazol was reported to unmask latent systemic lupus erythematosus in a male patient treated for angioneurotic edema. Fretwell et al, *J. Allergy Clin. Immunol.* 69: 306–310 (1982).

The use of progesterone in inhibiting immune clearance of antibody-coated cells from the circulation, and therefore its use in treating autoimmune disorders such as systemic lupus erythematosus, immune hemolytic anemia and immune thrombocytopenic purpura, is unattractive because of progesterone's end-organ hormonal effects. What is needed is an agent having the immune clearance inhibiting activity of progesterone without the progestational end-organ hormonal effects of progesterone and the side-effects of danazol and cyproterone acetate.

SUMMARY OF THE INVENTION

A method of inhibiting the clearance of antibody-coated cells from the circulation of mammals is provided. An effective amount of a compound selected from the group consisting of 17-hydroxyprogesterone and 16-methylprogesterone, preferably 17-alpha-hydroxyprogesterone and 16-alpha-methylprogesterone, is administered. 17-Alpha-hydroxyprogesterone, or 4-pregnen-17-alpha-ol-3,20-dione, has the follow formula:

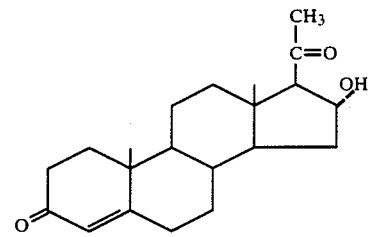

16-Alpha-methylprogesterone, or 4-pregnen-16-alpha-methyl-3,20-dione, has the following formula:

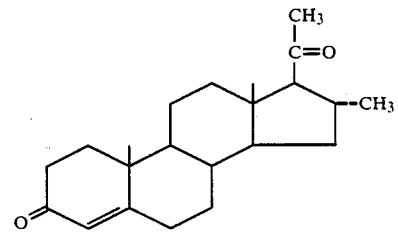

Administration of these compounds provides a method for inhibiting clearance of antibody-coated cells from the circulation of mammals, and thus provides a treatment for autoimmune disease.

DESCRIPTION OF THE FIGURE

The FIGURE is a plot of the clearance of the following $^{51}$Cr-radiolabeled cells from the circulation of experimental animals (guinea pigs) as a function of time:

uncoated guinea pig erythrocytes from untreated animals (open circle data points);

IgG-coated guinea pig erythrocytes from untreated animals (open square data points);

IgG-coated guinea pig erythrocytes from 17-alpha-hydroxyprogesterone-treated animals, 90 mg/kg/day (solid square data points) and 10 mg/kg/day (solid triangle data points).

DETAILED DESCRIPTION OF THE INVENTION

17-Alpha-hydroxyprogesterone is a naturally-occurring progesterone analogue. It may be prepared, for example, according to U.S. Pat. No. 2,648,662. 16-Alpha-methylprogesterone is a synthetic progesterone analog. Both of these compounds possess little, if any, glucocorticoid activity in vivo and in vitro. DiSorbo et al, *Ann. N.Y. Acad. Sci.* 206: 355-368 (1977). It has been established that 17-alpha-hydroxyprogesterone has lower uterine receptor affinity and progestogen activity than progesterone. Terenius et al, *Steroids* 23(6): 909-919 (1974). Surprisingly, I have found that this compound, while substantially lacking the end-organ hormonal effects of progesterone, retains the immune clearance inhibiting activity of progesterone. I have also found that 16-methylprogesterone, another progesterone analogue, has similar immune clearance inhibiting activity.

The immune clearance inhibiting activity of 17-hydroxyprogesterone and 16-methylprogesterone, and thus their utility in treating autoimmune disorders, is demonstrated as follows by an animal model of immune hemolytic anemia established by Schreiber, et al, *J. Clin. Invest.* 51: 575 (1972). This animal model has helped to elucidate the effect of corticosteroids in inhibiting the clearance of antibody-coated cells in vivo.

Progesterone, 17-alpha-hydroxyprogesterone and 16-alpha-methylprogesterone were each reconstituted in a steroid suspending vehicle consisting of 0.5% carboxylmethylcellulose, 0.4% Tween 80, and 1.5% ethanol in isotonic saline as described by Friedman et al, *J. Clin. Invest.* 75: 162-167 (1985). The two progesterone analogues were obtained from Steraloids, Inc. (Wilton, N.H.) Male and non-pregnant females (Hartley guinea pigs weighing 500-600 g, Dutchland Farms, Denver, Pa.) received injections of equal volumes of one of the steroid preparations or 1 ml of a sham preparation consisting of the steroid suspending vehicle without steroid. All animals were injected subcutaneously in the dorsal neck fat pad.

The clearance of IgG-coated erythrocytes was determined in all animals using erythrocytes sensitized with rabbit anti-guinea pig erythrocyte antibody. Rabbit IgG and IgM anti-guinea pig erythrocyte antibody was prepared in rabbits according to standard procedures. The IgG fraction was isolated by Sephadex G200 chromatography. Friedman et al, *J. Clin. Invest.* 75: 162-167 (1985). Guinea pig erythrocytes were obtained by cardiac puncture, washed, and radiolabeled with $^{51}$Cr-sodium chromate (New England Nuclear, Boston, MA). An aliquot of the radiolabeled erythrocytes was sensitized with rabbit antiguinea pig erythrocyte IgG antibody so as to coat each cell with approximately 6,000 molecules of IgG antibody per erythrocyte.

$2.7 \times 10^8$ antibody-coated or control radiolabeled red blood cells were injected intravenously into steroid- or sham-treated animals. Samples of blood were obtained from the retroorbital space 5-120 minutes after injection, and the radioactivity of each sample was measured using a gamma counter (Gamma 8000, Beckman Instruments, Inc., Fullerton, Calif.). The percentage of inhibition of clearance of antibody-coated cells is calculated according to the formula:

$$\% \text{ Inhibition of Clearance by Drug} = \left(1 - \frac{cpm_c - cpm_x}{cpm_c - cpm_{ea}}\right) \times 100$$

wherein $cpm_c$ is the blood radioactivity in counts per million of untreated control animals injected with unsensitized cells.

$cpm_x$ is the blood radioactivity in counts per million of steroid-treated animals injected with sensitized cells; and $cpm_{ea}$ is the blood radioactivity in counts per million of the sham-treated animals receiving sensitized cells.

The above formula compares immune clearance in treated animals and untreated animals studied on the same experimental days. The data is expressed as a percent alteration of clearance, where 100% inhibition of clearance by a steroid corresponds to the situation in which the clearance of antibody-sensitized erythrocyte ($cpm_x$) is identical to that of unsensitized erythrocytes ($cpm_c$). It is readily understood that if the effect of a steroid treatment is identical to the sham treatment, the mathematical expression is zero.

Animals were treated for seven days with (i) 10 mg/kg/day progesterone, (ii) 90 mg/kg/day progesterone (iii) 10 mg/kg/day 17-alpha-hydroxyprogesterone, (iv) 90 mg/kg/day 17-alpha-hydroxyprogesterone, and (v) steroid suspending vehicle (sham).

Guinea pigs treated with progesterone for 7 days exhibited impaired splenic clearance of IgG coated erythrocytes. Pretreatment with 90 mg/kg of progesterone inhibited the clearance of IgG coated erythrocytes in 6/6 animals ($p<0.05$) by $43\pm7\%$ compared with simultaneous sham treated controls. At 2 hours, $50\pm4\%$ of the IgG coated erythrocytes remained in the circulation in the progesterone treated animals compared with $28\pm4\%$ in sham controls.

The effect of 17-alpha-hydroxyprogesterone on the clearance of IgG-coated erythrocytes is compared to sham-treated controls in the FIGURE. The data in the FIGURE is expressed as mean $\pm$ SEM. Alteration of immune clearance was evaluated statistically at 90 and 120 minutes by two-tailed analysis using exact binomial possibilities where the expected result by chance random assortment would be 50% positive and 50% negative.

Pretreatment for 5-7 days with 90 mg/kg/day of 17-alpha-hydroxyprogesterone impaired immune clearance in 6/7 animals ($p<0.05$) by $40\pm10\%$ compared with simultaneously treated sham controls (FIGURE). Animals treated with 17-alpha-hydroxyprogesterone for 5-7 days at 10 mg/kg/day also demonstrated impaired clearance (5/6 guinea pigs by $41\pm10\%$; $p<0.05$). At 2 hours, $54\pm5\%$ of the IgG coated cells from animals treated with 90 mg/kg and $58\pm8\%$ of the cells from animals treated with 10 mg/kg remained in the circulation, compared to $44\pm7\%$, in sham controls (FIGURE).

Data from experiments using 16-alpha-methylprogesterone indicates that this analogue also inhibits splenic clearance of IgG-coated cells. At 2 hours, $56\pm11\%$ of cells in animals treated with 16-alphamethylprogesterone (90 mg/kg) remained in the circulation, compared with 45±10% of the cells in the simultaneously treated sham controls.

The results indicate that animals receiving the progesterone analogue 17-alpha-hydroxyprogesterone have impaired immune clearance compared to sham-treated controls to substantially the same extent as progesterone, notwithstanding the lack of progestational effect. Animals receiving 16-alpha-methylprogesterone exhibited a somewhat lesser impairment of immune clearance.

The compounds may be administered in dosages of about 1.0 mg/kg/day to about 90 mg/kg/day.

Immune clearance of antibody-coated cells may be achieved by administering the subject compounds by any convenient route. While parenteral administration is preferred, the compounds may be formulated for oral administration in the form of capsules, tablets, or the like.

The validity of the herein described guinea pig model for assessing the activity of a drug in treating autoimmune disease has been established. For example, data from this model evidencing inhibition of immune clearance by glucocorticoids agrees with the clinical observation in human disease. Patients with autoimmune hemolytic anemia or immune thrombocytopenic purpura treated with glucocorticoids often respond within days of the onset of therapy.

The autoimmune hemolytic anemias represent a group of disorders in which individuals produce antibodies directed to one or more of their own erythrocyte membrane antigens Coating of erythrocytes by antibodies is followed by their clearance from the circulation by splenic macrophages, and subsequent destruction in the spleen. As with human erythrocytes, guinea pig erythrocytes sensitized with IgG antibodies are cleared by macrophages in the spleen. Because of such similarities to man, the guinea pig is an accepted animal model for experimental study of autoimmune diseases, in particular autoimmune hemolytic anemia.

It is believed that 17-hydroxyprogesterone and 16-methylprogesterone are useful in treating autoimmune disorders such as immune hemolytic anemia, immune thrombocytopenic purpura, and perhaps autoimmune neutropenia. They may also prove to be useful in treating other autoimmune disorders such as systemic lupus erythematosus and rheumatoid arthritis.

The dosage and dosage regimen is selected to result in clinical response. For example, in the case of autoimmune hemolytic anemia or immune thrombocytopenic purpura, clinical response is evidenced by a rise in blood count.

Once a clinical response is achieved and the patient stabilizes, tapering of treatment should begin. This may take several months. Alternate day therapy may be effective in some patients after the clinical course of the disease stabilizes.

The present invention may be embodied in other specific forms without departing from the spirit or essential attributes thereof and, accordingly, reference should be made to the appended claims, rather than to the foregoing specification, as indicating the scope of the invention.

I claim:

1. A method of inhibiting the clearance of antibody-coated cells from the circulation of mammals comprising administering to a mammal exhibiting undesired clearance of antibody-coated cells an effective amount of a compound selected from the group consisting of 17-hydroxyprogesterone and 16-methylprogesterone.

2. A method according to claim 1 wherein the compound is 16-alpha-methylprogesterone.

3. A method according to claim 1 wherein the compound is 17-alpha-hydroxyprogesterone.

4. A method according to claim 2 wherein the dose of the compound is from about 1 mg/kg/day to about 90 mg/kg/day.

5. A method according to claim 3 wherein the dose of the compound is from about 1 mg/kg/day to about 90 mg/kg/day.

6. A method of treating immune throbocytopenic purpura comprising administering to a mammal having such disease an effective amount of a compound selected from the group consisting of 17-hydroxyprogesterone and 16-methylprogestrone.

7. The method of claim 6 wherein the compound is 17-hydroxyprogesterone.

8. The method of claim 6 wherein the compound is 16-methylprogesterone.

9. The method of claim 6 wherein said amount is from about 1 mg/kg/day to about 90 mg/kg/day.

10. A method of treating immune hemolytic anemia comprising administering to a mammal having such disease an effective amount of a compound selected from the group consisting of 17-hydroxyprogestrone and 16-methylprogestrone.

11. The method of claim 10 wherein the compound is 17-hydroxyprogesterone.

12. The method of claim 10 wherein the compound is 16-methylprogesterone.

13. The method of claim 10 wherein said amount is from about 1 mg/kg/day to about 90 mg/kg/day.

* * * * *